United States Patent
Kikta

(10) Patent No.: US 7,718,126 B2
(45) Date of Patent: *May 18, 2010

(54) FECAL OCCULT TEST PACKAGING

(76) Inventor: Kevin Kikta, 12 Crowel Rd., Hillsborough, NJ (US) 08844

( * ) Notice: Subject to any disclaimer, the term of this patent is extended or adjusted under 35 U.S.C. 154(b) by 0 days.

This patent is subject to a terminal disclaimer.

(21) Appl. No.: 12/477,878

(22) Filed: Jun. 3, 2009

(65) Prior Publication Data

US 2009/0238720 A1 Sep. 24, 2009

Related U.S. Application Data

(63) Continuation of application No. 11/558,882, filed on Nov. 10, 2006, now Pat. No. 7,556,769.

(51) Int. Cl.
*G01N 33/72* (2006.01)
*G01N 31/22* (2006.01)
*G01N 21/03* (2006.01)
*G01N 21/77* (2006.01)

(52) U.S. Cl. ............... 422/58; 422/55; 422/56; 422/61; 422/99; 436/63; 436/66; 436/164; 436/165; 436/169; 436/170; 206/459.1; 206/569; 435/287.1; 435/287.6

(58) Field of Classification Search ............ 436/63, 436/66, 164, 165, 169, 170; 422/55, 56, 422/58, 60, 61, 99, 102; 206/459.1, 569; 435/287.1, 287.6

See application file for complete search history.

(56) References Cited

U.S. PATENT DOCUMENTS

| | | | | |
|---|---|---|---|---|
| 3,996,006 A | * | 12/1976 | Pagano | 422/50 |
| 4,225,557 A | * | 9/1980 | Hartl et al. | 422/56 |
| 4,365,970 A | * | 12/1982 | Lawrence et al. | 436/66 |
| 4,511,533 A | * | 4/1985 | Guadagno et al. | 422/61 |
| 4,562,043 A | * | 12/1985 | Mennen et al. | 422/56 |
| 4,582,685 A | * | 4/1986 | Guadagno et al. | 422/61 |
| 4,645,743 A | * | 2/1987 | Baker et al. | 436/66 |
| 4,647,541 A | * | 3/1987 | Guadagno et al. | 436/66 |
| 4,789,629 A | * | 12/1988 | Baker et al. | 435/7.92 |
| 4,983,416 A | * | 1/1991 | Hunsinger et al. | 427/2.13 |
| 5,100,619 A | * | 3/1992 | Baker et al. | 422/58 |
| 5,182,191 A | * | 1/1993 | Fan et al. | 435/7.9 |
| 5,264,181 A | * | 11/1993 | Schreiber | 422/58 |
| 5,391,498 A | * | 2/1995 | Baker et al. | 436/66 |
| 5,840,584 A | * | 11/1998 | Waldenburg | 436/66 |
| 6,077,711 A | * | 6/2000 | Singer | 436/66 |
| 6,436,714 B1 | * | 8/2002 | Clawson et al. | 436/66 |

(Continued)

*Primary Examiner*—Maureen M Wallenhorst
(74) *Attorney, Agent, or Firm*—Jennifer Meredith; Meredith & Keyhani, PLLC

(57) ABSTRACT

A specimen testing device having a folding top having a top inside and a top outside; a back portion having a back inside and a back outside, the back portion in folding communication with the folding top; a front portion in folding communication with the back portion and the folding top covers at least a portion of the front portion when the front portion is in a folded closed position; a reagent test sheet in communication with at least a portion of the back portion; at least one enclosed bubble containing developer attached to at least one of the back portion and the front portion, wherein a fecal sample is placed on the reagent test sheet and the at least one enclosed bubble is pierced to release the developer to the fecal sample to indicate the presence of fecal occult blood.

19 Claims, 4 Drawing Sheets

U.S. PATENT DOCUMENTS

| | | | |
|---|---|---|---|
| 7,189,356 B1 * | 3/2007 | Clawson | 422/56 |
| 7,556,769 B2 * | 7/2009 | Kikta | 422/58 |
| 2005/0164397 A1 * | 7/2005 | Waldenburg | 436/66 |
| 2006/0018789 A1 * | 1/2006 | LaStella | 422/58 |
| 2008/0131971 A1 * | 6/2008 | Clawson | 436/66 |

* cited by examiner

FECAL OCCULT TEST PACKAGING

This application is a continuing application of application number 11558882 filed Nov. 10, 2006, now U.S. Pat. No. 7,556,169 issued on Jul. 7, 2009, entitled "Fecal Occult Test Packaging" which is incorporated herein by reference. The present invention relates to packaging for the handling and detection of fecal occult blood.

It is well know that colorectal cancer and large polyps bleed into the stool. Fecal occult blood may provide a reliable diagnostic indicator of a variety of medical conditions involving gastrointestinal bleeding which may otherwise be difficult to detect, including colorectal cancer. The use of this method is well described in the medical literature. See e.g., Greegor, D. H., Cancer 19; 330-337 (1969) and Hastings, J. B., Amer. J. Surg. 127:228-233 (1974). Tests for fecal occult blood based upon the oxidation of guaiac to form a blue colored product in the presence of hydrogen peroxide and hemoglobin have been described in U.S. Such products are sold under the trademarks HEMOCCULT® and SERAC-ULT®. Briefly, the test involves placing a fecal sample on an absorbent paper coated with guaiac and adding a developer solution containing hydrogen peroxide. If hemoglobin is present, the guaiac is oxidized, turning the paper blue. Another test involved the use of a paper coated with o-tolidine and a developer of peroxide. Different reagents may be used as they provide different levels of sensitivity to avoid false positives.

The problem with these products is that there may be numerous folding slides around an office, but only one or two bottles of developer. This can cause many problems including not being able to locate the single bottle of developer, contamination from numerous people touching the bottle and finally that physicians may want to give a slides to a patient for self testing, but can't give each of them an entire bottle of developer as they may only have a single bottle. Also, if the physician or nurse wants to use two different solutions to test the patients slide, they must separately find and open two bottles and drop the solutions on the slide. This is time consuming.

Accordingly, the present invention provides a self contained device that does not require a separate bottle of developer and may provide separate bubbles each containing different developers.

SUMMARY OF THE INVENTION

The present invention relates generally to devices for evaluating the presence of fecal occult blood.

According to one embodiment, a specimen testing device, comprising: a folding top having a top inside and a top outside; a back portion having a back inside and a back outside, the back portion in folding communication with the folding top; a front portion, wherein the front portion is in folding communication with the back portion and the folding top covers at least a portion of the front portion when the front portion is in a folded closed position; a reagent test sheet in communication with at least a portion of the back portion; at least one enclosed bubble containing developer attached to at least one of the back portion and said front portion, wherein a fecal sample is placed on the reagent test sheet and the at least one enclosed bubble is pierced to release the developer to the fecal sample to indicate the presence of fecal occult blood.

According to another embodiment, a specimen testing device, comprising: a folding top having a top inside and a top outside; a back portion having a back inside, back outside and at least one flap opening, the back portion in folding communication with the folding top; a front portion having at least one opening, wherein the front portion is in folding communication with the back portion and the folding top covers at least a portion of the front portion when the front portion is in a folded closed position; a reagent test sheet in communication with at least a portion of the back portion; at least one enclosed bubble containing developer attached to at least one of the flap opening of the back portion, back portion and the front portion; wherein a fecal sample is placed on the reagent test sheet and the at least one enclosed bubble is pierced to release the developer to the fecal sample to indicate the presence of fecal occult blood.

These and other features, aspects and advantages of the present invention will become better understood with reference to the following description and claims.

DETAILED DESCRIPTION OF THE INVENTION

Figure 1:
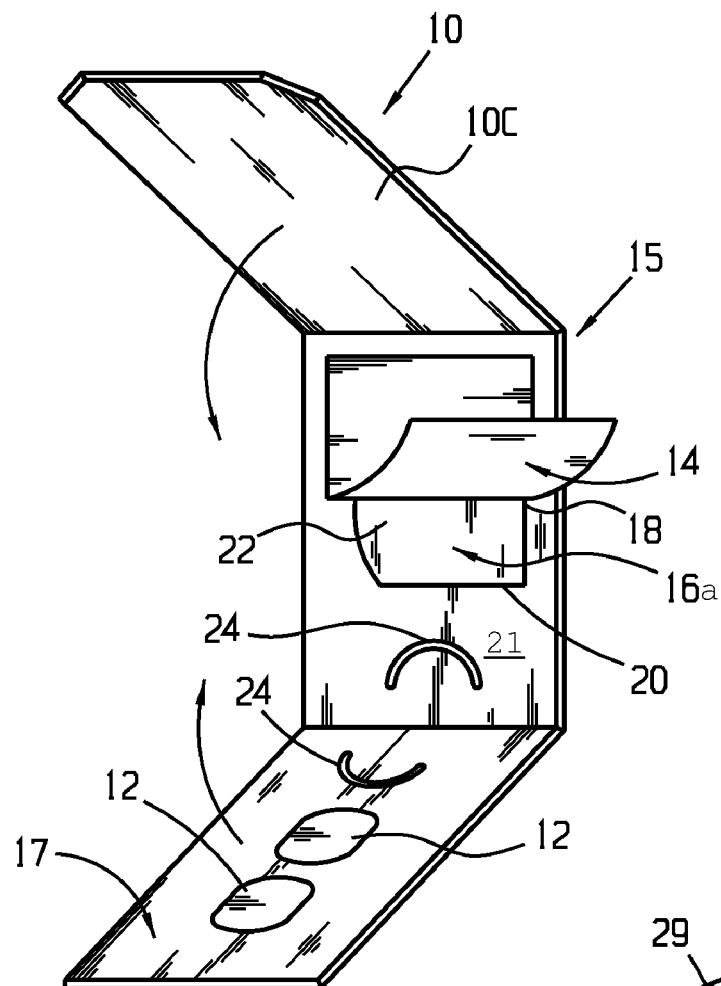
FIG. 1 depicts the present invention.

The following detailed description is of the best currently contemplated modes of carrying out the invention. The description is not to be taken in a limiting sense, but is made merely for the purpose of illustrating the general principles of the invention, since the scope of the invention is best defined by the appended claims.

As shown in FIGS. 1-9, the present invention provides a specimen testing device (10) having a folding top (10) having a top inside (10c) and a top outside (10d); a back portion (15) having a back inside (21) and back outside (23). There may also be least one flap opening (22). The back portion (15) may be in folding communication with the folding top (10). The front portion (17) may have at least one opening (12) with the folding top (10) covering at least a portion of the front portion (17) and the front portion (17) may be in folding communication with the back portion (15). The opening (12) in the front portion (17) is intended to allow for receipt of the fecal sample through the opening onto reagent test sheet (14) which is behind the opening (12) when the specimen testing device is in a folded closed position. The reagent test sheet (14) may be affixed to the back portion (15) with the reagent test sheet (14) interposed between the front portion (17) and the back portion (15). The reagent test sheet may be, for example, guaiac-impregnated paper. An enclosed bubble (30) containing developer may be attached to the back inside (21) or the inside (16a) of the flap opening (16) of the back portion (15) or even a portion of the front portion (17). An enclosed bubble (30) may be a bubble chamber created by, for example, two thin-films (or a single thin-film folded over) with an enclosed chamber containing developer which creates the bubble. The enclosed chamber may be any shape (tear drop, circular, etc.) and the resulting enclosed bubble may also be of any desired shape. The thin film may be a thermoplastic, for example, that is peripherally sealed upon injection of the developer. It should be understood that the opening of the back portion (15) does not need to have a flap opening (16).

Figure 2:
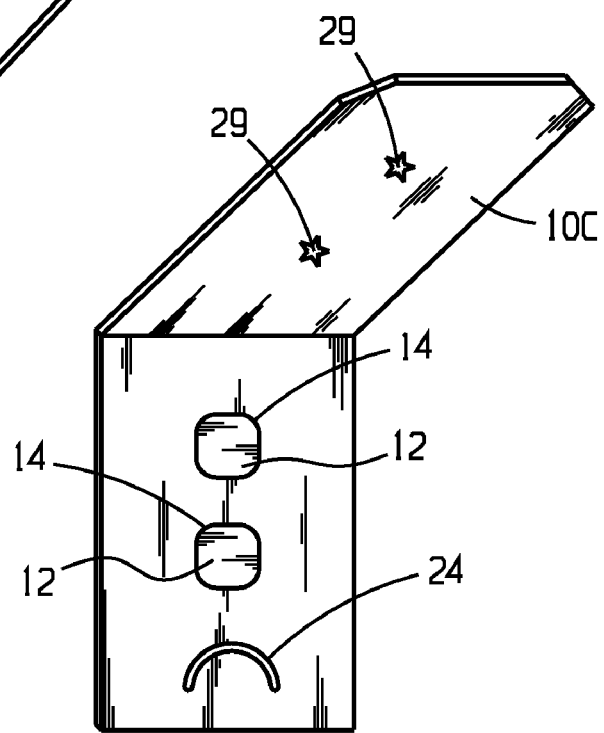
FIG. 2 depicts the present invention.
Figure 3:
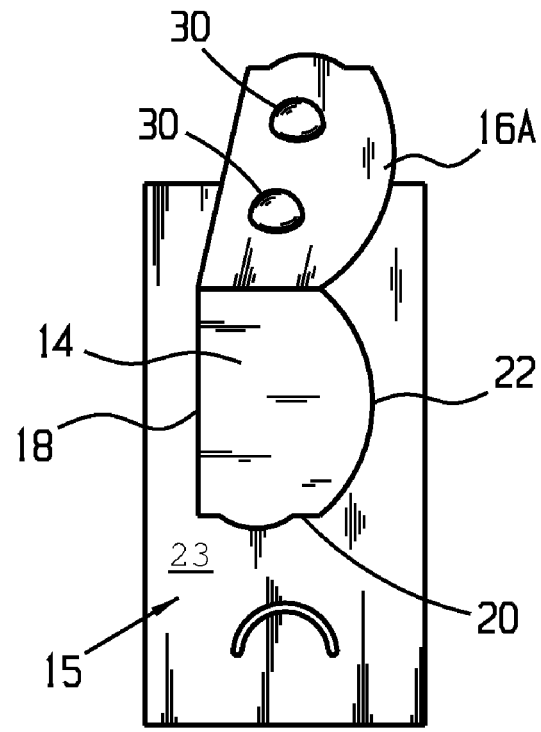
FIG. 3 depicts the present invention.
Figure 4:
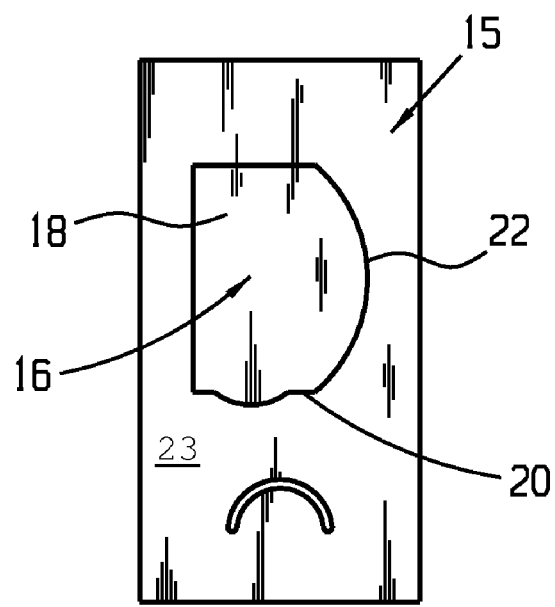
FIG. 4 depicts the present invention.
Figure 5:
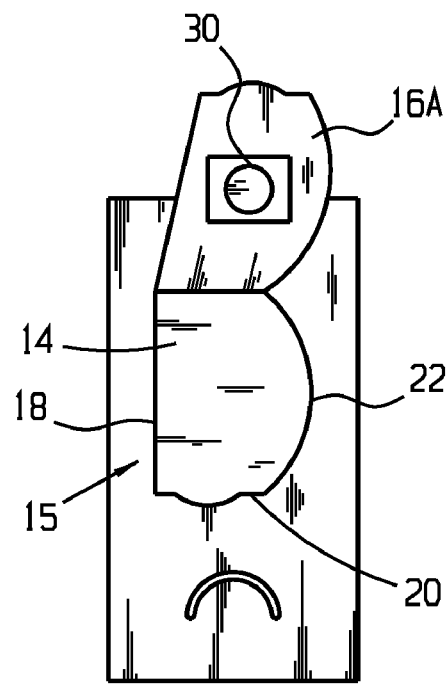
FIG. 5 depicts the present invention.
Figure 6:
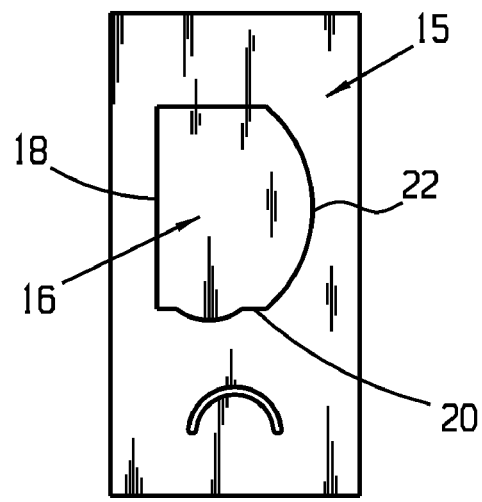
FIG. 6 depicts the present invention.
Figure 7:
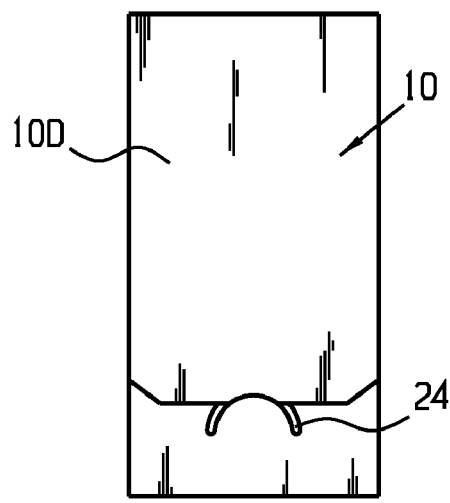
FIG. 7 depicts the present invention.
Figure 8:
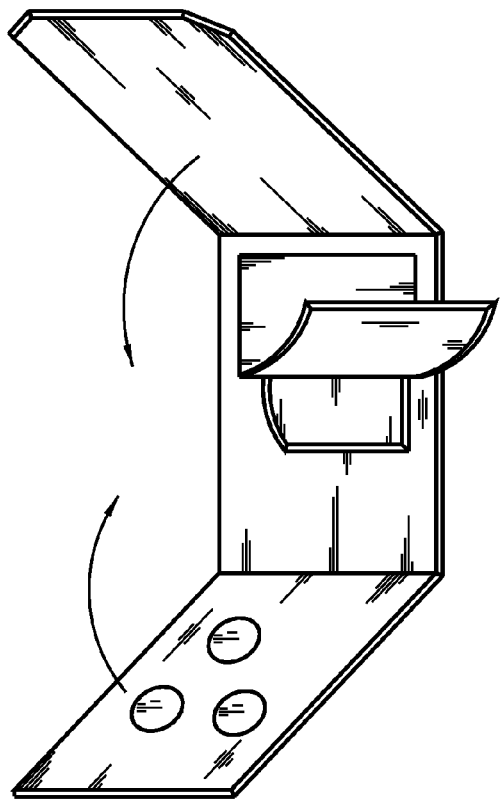
FIG. 8 depicts the present invention.
Figure 9:
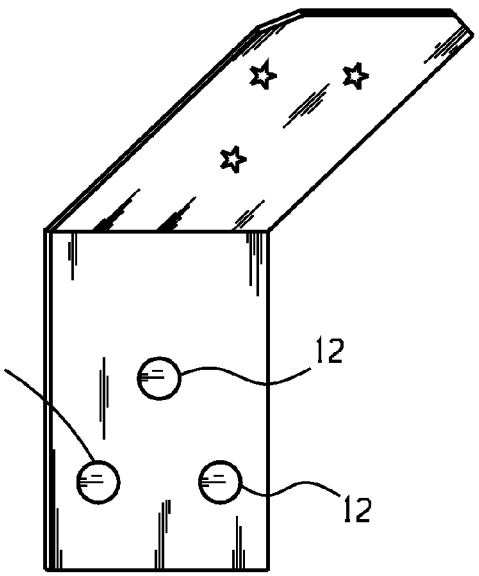
FIG. 9 depicts the present invention.
Figure 10:
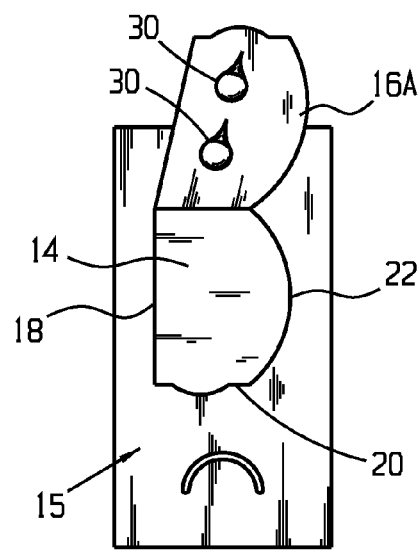
FIG. 10 depicts the present invention.

However, this is useful, as the enclosed bubble (30) when attached to the flap opening (16) may be kept in an open position to avoid the enclosed bubble (30) from inadvertently releasing the developer. There may also be a raised portion (29) on the top inside (10c) directly opposing the enclosed bubble (30) when the folding top is in a closed position. The raised portion (29) may be separated from the enclosed bubble by the reagent test sheet (14). The enclosed bubble may be pierced to release the developer by pressure on a portion of the thin film (similar to popping bubble wrap). The raised portion (29) may also be sharp and/or pointed, to aid in puncturing (or piercing) the enclosed bubble (30) to release the developer. The developer may be a stabilized aqueous solution of 5% hydrogen peroxide and 75% ethanol. According to another embodiment, the reagent test sheet is an oxidizable substrate that produces a colored product in the presence of peroxide and hemoglobin and the developer is a hydrogen peroxide or a peroxide source; and an enhancer selected from the group consisting of monocyclic nitrogen-containing aromatic heterocyclic compounds or tertiary or quaternary ammonium compounds which enhance the sensitivity of the test. According to another embodiment, the developer generally contains 4 to 6% by weight of hydrogen peroxide, 0.2 to 4% by weight of the enhancer, and 80 to 90% ethanol with the balance being water. This developer solution contains hydrogen peroxide or a source of peroxide such as cumene hydroperoxide and the enhancer in an ethanol/water carrier. Enhancers useful in the present invention include monocyclic nitrogen-containing aromatic heterocyclic compounds such as triazole, pyridine, pyrazine and substituted derivatives thereof, including 4-benzyl pyridine, 2-methoxy pyridine, 4-(p-nitrobenzyl) pyridine, and pyrazine carboxylic acid. Other enhancers in accordance with the invention are tertiary or quaternary amines having at least one hydroxy alkyl or esterified hydroxy alkyl group attached to the nitrogen. Examples of such enhancers include diethyl ethanolamine, ethyl diethanolamine and triethanolamine, acetylcholine chloride and .beta.-methyl acetylcholine chloride. A further class of enhancers in accordance with the present invention are tertiary and quaternary amines having a phenyl group attached to the nitrogen, e.g. dimethyl aniline. Quinoline and derivatives thereof such as alpha-hydroxy quinoline were also found to be effective enhancers. It should be understood that the developer may be any other developer known within the art of fecal occult testing. There may also be more than one enclosed bubble (30) and each enclosed bubble (30) may contain a different developer. The enclosed bubble may be a sheet of thin film plastic, such as polyethylene, comprising a multiplicity of individual closed cell compartments, each of the closed cell compartments being substantially raised and spherical and containing an amount of developer. This is particularly desirable as different developers may provide different levels of accuracy. The at least one opening (12) of the front portion (17) may be two aligned round openings (as shown in FIGS. 1-2). There may be a hydrophobic barrier between the two aligned round openings, to prevent flow of the released developer between the two aligned round openings. The at least one opening (12) of the front portion (17) may also be three openings (12) forming a triangular shape (as shown in FIGS. 8-9). There may also be a hydrophobic barrier surrounding the at least one flap opening of the back portion. There may also be an indicator such as a plus sign (as shown in FIG. 2) printed on the reagent test strip (14) in the center of the at least one opening (12). A fecal sample may be placed on the indicator and the folding top (10) closed. Pressure may then be placed on the middle of the specimen testing device, bursting the enclosed bubble (30), releasing the developer to indicate the presence of fecal occult blood. The fecal sample may be placed directly on the reagent test sheet when the folding top and front portion are in an open position (as in FIGS. 1 and 8), or may be placed on the reagent test sheet through the openings in the front portion when the front portion is in a closed position (as in FIGS. 2 and 9). As depicted in FIG. 10, the bubble (30) may be tear drop shaped or any similar shape with a tail directing the fluid to a particular spot.

It should be understood that the foregoing relates to preferred embodiments of the invention and that modifications may be made without departing from the spirit and scope of the invention as set forth in the following claims.

I claim:
1. A specimen testing device, comprising:
a folding top having a top inside and a top outside;
a back portion having a back inside and a back outside, said back portion in folding communication with said folding top;
a front portion, wherein said front portion is in folding communication with said back inside of said back portion and said folding top covers at least a portion of said front portion when said front portion is in a folded closed position;
a reagent test sheet in communication with at least a portion of said back portion; and
at least one enclosed bubble containing developer attached to at least one of said back portion and said front portion,
wherein a fecal sample is placed on said reagent test sheet and said front portion folded over said back inside of said back portion and said folding top folded over said front portion so that said folding top covers at least a portion of said front portion to provide said front portion in a folded closed position and said at least one enclosed bubble is pierced to release said developer onto said reagent test sheet to indicate the presence of fecal occult blood in said fecal sample placed on said reagent test sheet.

2. A specimen testing device as in claim 1, wherein said top inside has a raised portion directly opposing said at least one enclosed bubble when said folding top is in a closed position.

3. A specimen testing device as in claim 1, wherein said developer is a stabilized aqueous solution of hydrogen peroxide and ethanol.

4. A specimen testing device as in claim 1, wherein each said at least one enclosed bubble contains a different developer.

5. A specimen testing device as in claim 1, further comprising at least one opening in said front portion, wherein said at least one opening is two aligned round openings to allow for receipt of said fecal sample through said opening onto said reagent test sheet and said front portion folded over said back portion and said folding top folded over said front portion so that said folding top covers at least a portion of said front portion to provide said front portion in a folded closed position.

6. A specimen testing device as in claim 1, further comprising at least one opening in said front portion, wherein said at least one opening is two aligned round openings and further comprising a hydrophobic barrier between said two aligned round openings.

7. A specimen testing device as in claim 1, further comprising at least one opening in said front portion, wherein said at least one opening of said front portion is three openings forming a triangular shape.

8. A specimen testing device as in claim 1, wherein said back portion has a flap opening and further comprising a hydrophobic barrier surrounding said at least one flap opening of said back portion.

9. A specimen testing device as in claim 1, further comprising an indicator printed on said reagent test sheet.

10. A specimen testing device as in claim 1, wherein said at least one enclosed bubble is tear drop shaped.

11. A specimen testing device, comprising:

a folding top having a top inside and a top outside;

a back portion having a back inside, back outside and at least one flap opening, said back portion in folding communication with said folding top;

a front portion having at least one opening, wherein said front portion is in folding communication with said back inside of said back portion and said folding top covers at least a portion of said front portion when said front portion is in a folded closed position;

a reagent test sheet in communication with at least a portion of said back portion;

at least one enclosed bubble containing developer attached to at least one of said flap opening of said back portion, back portion and said front portion;

wherein a fecal sample is placed on said reagent test sheet and said front portion folded over said back inside of said back portion and said folding top folded over said front portion so that said folding top covers at least a portion of said front portion to provide said front portion in a folded closed position and said at least one enclosed bubble is pierced to release said developer onto said reagent test sheet to indicate the presence of fecal occult blood in said fecal sample placed on said reagent test sheet.

12. A specimen testing device as in claim 11, further comprising a raised portion on the top inside directly opposing the enclosed bubble when the folding top is in a closed position wherein said raised portion has a pointed tip directly opposing said at least one enclosed bubble containing developer.

13. A specimen testing device as in claim 11, wherein each said at least one enclosed bubble contains a different developer.

14. A specimen testing device as in claim 11, wherein said at least one opening in said front portion is two aligned round openings.

15. A specimen testing device as in claim 11, wherein said at least one opening in said front portion is two aligned round openings and further comprising a hydrophobic barrier between said two aligned round openings.

16. A specimen testing device as in claim 11, wherein said at least one opening of said front portion is three openings forming a triangular shape.

17. A specimen testing device as in claim 11, further comprising a hydrophobic barrier surrounding said at least one flap opening of said back portion.

18. A specimen testing device as in claim 11, further comprising an indicator printed on said reagent test sheet in the center of said at least one opening.

19. A specimen testing device as in claim 11, wherein said at least one enclosed bubble is tear drop shaped.

* * * * *